(12) United States Patent
Glasnapp

(10) Patent No.: US 9,387,189 B2
(45) Date of Patent: Jul. 12, 2016

(54) ANTIBIOTIC COMPOSITION COMPRISING A CHEMOTACTIC AGENT AND A NUTRIENT DISPERSION

(71) Applicant: Professional Compounding Centers of America, Houston, TX (US)

(72) Inventor: Andrew B. Glasnapp, Sugar Land, TX (US)

(73) Assignee: Professional Compounding Centers of America (PCCA), Houston, TX (US)

(*) Notice: Subject to any disclaimer, the term of this patent is extended or adjusted under 35 U.S.C. 154(b) by 0 days.

(21) Appl. No.: 13/899,980

(22) Filed: May 22, 2013

(65) Prior Publication Data

US 2014/0348780 A1  Nov. 27, 2014

(51) Int. Cl.

| | | |
|---|---|---|
| *A61K 31/202* | (2006.01) | |
| *A61K 38/06* | (2006.01) | |
| *A61K 45/06* | (2006.01) | |
| *A61K 38/20* | (2006.01) | |
| *A61K 38/02* | (2006.01) | |
| *A23L 1/00* | (2006.01) | |
| *A61K 38/17* | (2006.01) | |
| *A61K 38/19* | (2006.01) | |
| *A61K 47/10* | (2006.01) | |
| *A61K 47/12* | (2006.01) | |
| *A61K 47/18* | (2006.01) | |
| *A61L 27/16* | (2006.01) | |
| *A61L 27/52* | (2006.01) | |
| *A61L 27/54* | (2006.01) | |
| *A61K 31/496* | (2006.01) | |
| *A61K 31/7036* | (2006.01) | |

(52) U.S. Cl.
CPC .............. *A61K 31/202* (2013.01); *A23L 1/00* (2013.01); *A61K 31/496* (2013.01); *A61K 31/7036* (2013.01); *A61K 38/06* (2013.01); *A61K 38/1725* (2013.01); *A61K 38/195* (2013.01); *A61K 38/2053* (2013.01); *A61K 45/06* (2013.01); *A61K 47/10* (2013.01); *A61K 47/12* (2013.01); *A61K 47/183* (2013.01); *A61L 27/16* (2013.01); *A61L 27/52* (2013.01); *A61L 27/54* (2013.01); *A61L 2430/00* (2013.01)

(58) Field of Classification Search
None
See application file for complete search history.

(56) References Cited

U.S. PATENT DOCUMENTS

| | | | | |
|---|---|---|---|---|
| 5,700,444 | A * | 12/1997 | Zamora et al. | 424/1.69 |
| 6,632,425 | B1 * | 10/2003 | Li et al. | 424/85.1 |
| 7,955,818 | B2 | 6/2011 | Bernardi et al. | |
| 2007/0202051 | A1 * | 8/2007 | Schuschnig | 424/45 |
| 2008/0249022 | A1 | 10/2008 | Grote et al. | |
| 2009/0117109 | A1 | 5/2009 | Thornthwaite et al. | |
| 2009/0232744 | A1 | 9/2009 | Keller et al. | |
| 2011/0039763 | A1 | 2/2011 | Eckert et al. | |
| 2011/0218139 | A1 | 9/2011 | Robinson et al. | |
| 2012/0121539 | A1 * | 5/2012 | Sands et al. | 424/85.2 |
| 2012/0321687 | A1 | 12/2012 | Hughes et al. | |

OTHER PUBLICATIONS

Graff, Jason R et al. "Vibrio Cholerae Exploits Sub-Lethal Concentrations of a Competitor-Produced Antibiotic to Avoid Toxic Interactions." Frontiers in microbiology 4 (2013): vol. 4, No. 8: 1-11.
Sommerfeld Ross, et al. "Nutrient Dispersion Enhances Conventional Antibiotic Activity Against . . . " Int'l Journal of Antimicrobial Agents 40.2 (2012): 177-181. NCBI PubMed. Web.

* cited by examiner

*Primary Examiner* — Brian J Gangle
*Assistant Examiner* — Andrew McCollum
(74) *Attorney, Agent, or Firm* — David G. Woodral, Esq.; Fellers, Snider, Blankenship, Bailey & Tippens, P.C.

(57) ABSTRACT

Compositions and methods for treating infectious diseases produced by biofilms are disclosed. More specifically, the present disclosure refers to pharmaceutical compositions which may be used for treating biofilm infections, specifically, biofilms formed by bacteria such as *Pseudomonas, E. coli, Klebsiella*, and other human pathogens. Pharmaceutical compositions may include a nutrient dispersion. Pharmaceutical compositions disclosed may employ chemotactic agents in order to disrupt biofilms and therefore enhance the antibiotic response. Pharmaceutical compositions disclosed may include suitable vehicles which may depend on the dosage form.

3 Claims, 1 Drawing Sheet

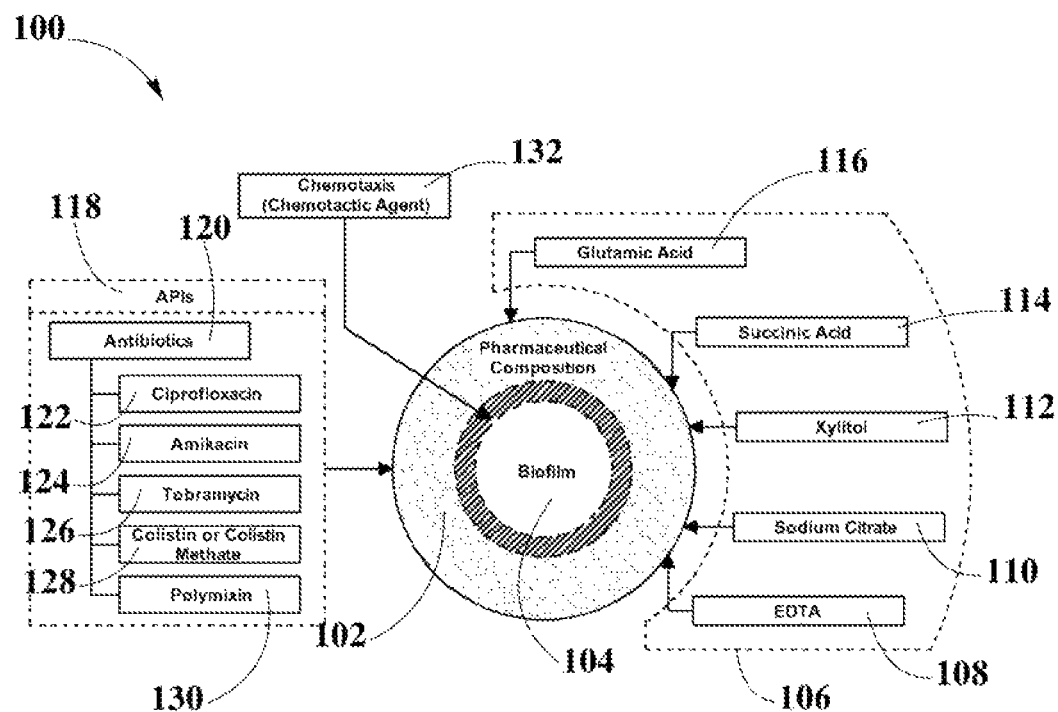

ANTIBIOTIC COMPOSITION COMPRISING A CHEMOTACTIC AGENT AND A NUTRIENT DISPERSION

CROSS-REFERENCE TO RELATED APPLICATIONS

N/A

FIELD OF THE DISCLOSURE

The present disclosure relates generally to microbial infections, and more particularly, to methods and compositions for treating bacterial biofilm using pharmaceutical compositions.

BACKGROUND

Bacterial biofilms cause significant infections in the medical field. Antibiotics commonly used to treat these infections often do not achieve complete bacterial eradication. New approaches to eliminate biofilms have focused on dispersion compounds to entice the bacteria to actively escape or disperse from the biofilm, where the bacteria may become more susceptible to antibiotics.

Current researches have identified the genes that may be specifically involved in increased resistance of biofilm cells, where there has been isolated several mutants of uropathogenic *Escherichia coli*, and *Staphylococcus aureus* and which form "normal" biofilms, but which do not possess increased resistance. The persistence of, for example, staphylococcal infections related to foreign bodies is due to biofilm formation. Likewise, chronic *Pseudomonas aeruginosa* lung infection in cystic fibrosis patients is caused by biofilm-growing mucoid strains. Furthermore, biofilm growth is associated with an increased level of mutations as well as with quorum-sensing-regulated mechanisms.

Characteristically, gradients of nutrients and oxygen exist from the top to the bottom of biofilms and these gradients are associated with decreased bacterial metabolic activity and increased doubling times of the bacterial cells; it is these more or less dormant cells that are responsible for some of the tolerance to antibiotics. Biofilms may be prevented by early aggressive antibiotic prophylaxis or therapy and may be treated by chronic suppressive therapy.

Moreover, a term that may be commonly used for chronic diseases as consequence of bacterial biofilms is bacterial chemotaxis. Specifically, chemotaxis may be described as the directed cell locomotion in concentration gradients of soluble extracellular agents. Substances that induce a chemotactic response (chemotactic factors) are known also under the general name of cytotaxin, chemotaxin, or chemo-attractants. Additionally, cells showing positive chemotaxis move towards areas with higher concentrations of chemotactic agents, while those showing negative chemotaxis moves away from these areas.

Numerous active pharmaceutical ingredients (APIs) such as antibiotics in combination with chemotactic agents have been studied in order to produce a pharmaceutical composition that could be effective in disrupting bacterial biofilms. However, there is no specific research that could provide a suitable dosage or concentration of antibiotics, chemotactic agent, or any other chemical agent to kill or eradicate the biofilms in different sites of human body.

There is therefore a need for pharmaceutical compositions that may include chemotactic agents combined with APIs, such as antibiotics, and other ingredients that could be effective for disrupting bacterial biofilms or microbial colonies.

Therefore, various dosage forms of the pharmaceutical composition that include chemotactic agents may be used for treating some chronic diseases.

SUMMARY

According to various embodiments, the present disclosure relates to compositions and methods for treating infectious diseases produced by biofilms. More specifically, the present disclosure refers to a pharmaceutical composition that may be administrated in dosage form such as mouth rinses, nasal sprays, solutions, oral solutions, inhalation solution, oral liquids suspensions, and capsules, among others. The pharmaceutical compositions may be used for disrupting bacterial biofilms, specifically, biofilms formed by bacteria such as *Pseudomonas, E. coli, Klebsiella*, and other human pathogens.

According to one embodiment, the pharmaceutical composition may be used for disrupting biofilms formed in chronic infections such as bacterial vaginosis, chronic nasal and sinus infections (sinusitis, chronic rhinosinusitis), oral and dental infections (periodontal diseases such as chronic periodontitis), cystic fibrosis, and chronic gangrene (by infection or ischemia), among others.

According to one embodiment, the pharmaceutical composition may include a nutrient dispersion that may include compounds such as, sodium citrate, succinic acid, xylitol, glutamic acid, and ethylenediaminetetraacetic acid (EDTA). In addition, the pharmaceutical composition may include APIs such as antibiotic agents.

Some embodiments may include antibiotic agents such as ciprofloxacin, amikacin, tobramycin, colistin methate, and polymixin, among others. Specifically, the pharmaceutical composition may include about 1 mM to about 100 mM of sodium citrate, most suitable may be about 10 mM of sodium citrate; about 7.5 mM to about 300 mM of xylitol, most suitable may be 75 mM of xylitol; about 1 mM to about 100 mM of glutamic acid, most suitable may be 10 mM of glutamic acid; about 0.1% by weight to about 10% by weight of EDTA, and about 0.1% by weight to about 5.0% by weight of ciprofloxacin (antibiotic).

In one embodiment, the pharmaceutical composition may include about 0.1% by weight to about 5.0% by weight of tobramycin as antibiotic agent. In further embodiments, the pharmaceutical composition may include about 0.1% by weight to about 5.0% by weight of colistin methate as antibiotic agent. In still further embodiments, the pharmaceutical composition may include 0.1% by weight to about 5.0% by weight of polymixin as antibiotic agent.

In one embodiment, the pharmaceutical composition may include suitable vehicles which may depend on the dosage form, where suitable vehicle ingredients may be poloxamers, water, propylene glycol, polyethylene glycol, fatty acids, methylcellulose, oils, starch, petroleum derivatives such as mineral oil and white petrolatum, lactose, gums, microcrystalline cellulose, and silicones, among others.

Pharmaceutical compositions may be used for disrupting bacterial biofilms via chemotaxis because pharmaceutical compositions may include chemotactic agents that may enhance the antibiotics activity. The chemotactic agents may be used as an energy source in a solution around the microbes (biofilm), subsequently, the microbes may change the proteins that they secrete. Consequently, the microbes may disrupt their own biofilm and move through the energy source, exposing themselves to the API (such as antibiotics) within the pharmaceutical composition.

Numerous other aspects, features and advantages of the present disclosure may be made apparent from the following detailed description taken together with the drawing figures.

BRIEF DESCRIPTION OF THE DRAWINGS

The present disclosure can be better understood by referring to the following figures. The components in the figures are not necessarily to scale, emphasis instead being placed upon illustrating the principles of the invention. In the figures, reference numerals designate corresponding parts throughout the different views.

FIG. 1 depicts a block diagram of a pharmaceutical composition for disrupting bacterial biofilms, according to an embodiment.

DETAILED DESCRIPTION

The present disclosure is herein described in detail with reference to embodiments illustrated in the drawings, which form a part here. In the drawings, which are not necessarily to scale or to proportion, similar symbols typically identify similar components, unless context dictates otherwise. Other embodiments may be used and/or other changes may be made without departing from the spirit or scope of the present disclosure. The illustrative embodiments described in the detailed description are not meant to be limiting of the subject matter presented herein.

As used here, the following terms may have the following definitions:

"Chemotaxis" refers to the characteristic movement or orientation of an organism/microorganism or cell along a chemical concentration gradient either toward or away from a chemical stimulus.

"Biofilm" refers to a structured consortium of bacteria embedded in a self-produced polymer matrix consisting of polysaccharides, protein and DNA.

"Active pharmaceutical ingredient" or "API" refers to a chemical compound that induces a desired pharmacological, physiological effect, and include agents that are therapeutically effective, prophylactically effective, or cosmeceutically effective.

"Treating" and "treatment" refers to a reduction in severity and/or frequency of symptoms, elimination of symptoms and/or underlying cause, prevention of the occurrence of symptoms and/or their underlying cause, and improvement or remediation of damage.

"Nutrient dispersion" refers to a dispersion of compounds that entice bacteria to actively escape or disrupt from the biofilm, where the bacteria may become more susceptible to antibiotics.

DESCRIPTION

FIG. 1 depicts block diagram 100 of pharmaceutical composition 102 for disrupting bacterial biofilm 104, according to an embodiment. More specifically, the pharmaceutical composition 102 may be used for disrupting biofilms 104 formed in chronic infections such as bacterial vaginosis, chronic nasal and sinus infections (sinusitis, chronic rhinosinusitis), oral and dental infections (periodontal diseases such as chronic periodontitis), cystic fibrosis, and chronic gangrene (by infection or ischemia), among others.

According to one embodiment, a pharmaceutical composition 102 may include nutrient dispersion 106 that includes compounds such as, sodium citrate 110, succinic acid 114, xylitol 112, glutamic acid 116, and EDTA 108. In addition, pharmaceutical compositions 102 may include APIs 118 such as antibiotic 120 agents. Some embodiments may include antibiotic 120 agents such as ciprofloxacin 122, amikacin 124, tobramycin 126, colistin methate 128, and polymixin 130, among others.

More specifically, pharmaceutical composition 102 may include about 1 mM to about 100 mM of sodium citrate 110, most suitable may be about 10 mM of sodium citrate 110; about 7.5 mM to about 300 mM of xylitol 112, most suitable may be 75 mM of xylitol 112; about 1.0 mM to about 100 mM of glutamic acid 116, most suitable may be 10 mM of glutamic acid 116; about 0.1% by weight to about 10% by weight of EDTA 108, and about 0.1% by weight to about 5.0% by weight of ciprofloxacin 122 (as an antibiotic 120 agent).

In one embodiment, pharmaceutical composition 102 may include about 0.1% by weight to about 5.0% by weight of tobramycin 126 as antibiotic 120 agent. In further embodiments, pharmaceutical composition 102 may include about 0.1% by weight to about 5.0% by weight of colistin methate 128 as antibiotic 120 agent. In still further embodiments, pharmaceutical composition 102 may include 0.1% by weight to about 5.0% by weight of polymixin 130 as antibiotic 120 agent.

In one embodiment, a pharmaceutical compositions 102 may include suitable vehicles which may depend on the dosage form, where suitable vehicles ingredients may be poloxamers, water, propylene glycol, polyethylene glycol, fatty acids, methylcellulose, oils, starch, petroleum derivatives such as mineral oil and white petrolatum, lactose, gums, microcrystalline cellulose, and silicones, among others.

Furthermore, a pharmaceutical composition 102 may disrupt bacterial biofilms 104 via chemotaxis because pharmaceutical compositions 102 may include chemotactic agents 132 in order to enhance antibiotics 120 activity. According to some embodiments, chemotactic agents 132 may be used as energy source in a solution around the bacteria within biofilm 104, such that, bacteria may change the proteins that they secrete. Consequently, the bacteria may disrupt their own biofilm 104 and move through the energy source, exposing themselves to a pharmaceutical composition 102 which may include antibiotics 120.

Chemotactic agents 132 may include for instance small proteins with a terminal formyl group, such as fMLP (N-formyl-Methionyl-Leucyl-Phenylalanine). Other chemotactic agents 132 may be activated complement factors (such as the anaphyloxins C3a and C5a), leukotrienes (such as Leukotriene B4 (LTB4) and Platelet-Activating Factor (PAF)); another group may be the chemokines produced by different cell types such as interleukin-8 (monocytes and endothelial cells), chemokine ligand 5 (CCL5 or also known as regulated upon activation normal T-cell expressed and secreted (RANTES)), eotaxin, monocyte chemotactic protein (MCP), and macrophage inflammatory protein (MIP), among others.

Antibiotic Agents

According to some embodiments antibiotic 120 agents may include: ampicillin, bacampicillin, carbenicillin indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin g, penicillin v, piperacillin tazobactam, ticarcillin clavulanic acid, nafcillin, cephalosporin i generation antibiotics, cefadroxil, cefazolin, cephalexin, cephalothin, cephapirin, cephradine cefaclor, cefamandol, cefonicid, cefotetan, cefoxitin, cefprozil, ceftmetazole, cefuroxime, loracarbef, cefdinir, ceftibuten, cefoperazone, cefixime, cefotaxime, cefpodoxime proxetil, ceftazidime, ceftizoxime, ceftriaxone, azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, mozzxifloxacin, nalidixic acid, norfloxacin, ofloxacin, sparfloxacin, trovafloxacin, oxolinic acid, gemifloxacin, perfloxacin, imipenem-cilastatin, meropenem, aztreonam, amikacin, gentamicin, kanamycin, neomycin, netilmicin, streptomycin, tobramycin, paromomycin, teicoplanin, vancomycin, demeclocycline, doxycycline, methacycline, minocycline, oxytetracycline, tetracycline, chlortetracycline, mafenide, silver sulfadiazine, sulfacetamide, sulfadiazine, sulfamethoxazole, sulfasalazine, sulfisoxazole, trimethoprim-sulfamethoxazole, sulfamethizole, rifabutin, rifampin, rifapentine, linezolid, streptogramins, quinopristin dalfopristin, bacitracin, chloramphenicol, fosfomycin, isoniazid, methenamine, metronidazol, mupirocin, nitrofurantoin, nitrofurazone, novobiocin, polymyxin, spectinomycin, trimethoprim, colistin, cycloserine, capreomycin, ethionamide, pyrazinamide, para-aminosalicyclic acid, erythromycin ethylsuccinate and combinations thereof.

Administration Route of the Pharmaceutical Composition

The most suitable route of pharmaceutical composition 102 may depend on the nature and severity of the condition being treated. In one embodiment, pharmaceutical composition 102 may be administrated in dosage form such as mouth rinses, nasal sprays, solutions, oral solutions, inhalation solution, gels, oral liquids suspensions, ointments, creams, ointments, anhydrous solutions, lotions, and capsules, among others. A pharmaceutical composition 102 may be used for disrupting biofilms 104 infections, specifically, in biofilms 104 formed by bacteria such as *Pseudomonas, E. coli, Klebsiella*, and other human pathogens. In an embodiment, the pharmaceutical composition can be administered to an animal, which can be a mammal. In an embodiment, a mammal is human.

In another embodiment, a pharmaceutical composition 102 may be administrated and manufactured by any suitable means known in the art, for example, topically (including via direct application to skin or to any epithelial tissue surface, including such surfaces as may be present in glandular tissues or in the respiratory and/or gastrointestinal tracts), vaginally, intraperitoneally, orally, parenterally, intravenously, intraarterially, transdermally, sublingually, subcutaneously, intramuscularly, transbuccally, intranasally, via inhalation, intraoccularly, subcutaneously, intraadiposally, and intraarticularly or intrathecally among others.

For instance, in topical administration the carrier may include a solution, emulsion, ointment or gel base. The base, for example, may include one or more components such as petrolatum, lanolin, polyethylene glycols, bee wax, mineral oil, diluents such as water and alcohol, and emulsifiers and stabilizers, among others.

According to some embodiments, topical administration may include direct application into an opened wound. For instance, an opened fracture or another opened wound may include a break in the skin that may expose additional underlying tissues to the external environment in a manner that renders them susceptible to microbial infection.

In one embodiment, topical formulation may be provided in the forms of a cream, lotion, solution, spray, gel, ointment, paste, micelles, microspheres and other microparticle/nanoparticle delivery elements, among others.

EXAMPLES

Example #1 is an application of a pharmaceutical composition 102, which may be used for disrupting a bacterial biofilm 104 in animals. Pharmaceutical compositions 102 for animals may be in any suitable dosage form such as mouth rinses, nasal sprays, solutions, oral solutions, inhalation solution, topical gels, creams, oral liquids suspensions, and capsules, among others.

Example #2 is an embodiment of pharmaceutical composition 102, which may include APIs 118 such as antibiotics 120 and antifungals.

While various aspects and embodiments have been disclosed here, other aspects and embodiments may be contemplated. The various aspects and embodiments disclosed here are for purposes of illustration and are not intended to be limiting, with the true scope and spirit being indicated by the following claims.

I claim:

1. An anti-biofilm composition, comprising:
   a) a chemotactic agent;
   b) a nutrient dispersion including about 1 mM to about 100 mM of sodium citrate, about 7.5 mM to about 300 mM of xylitol, and about 1.0 mM to about 100 mM of glutamic acid; and
   c) an antibiotic.

2. The composition of claim 1, wherein the nutrient dispersion includes about 10 mM glutamic acid.

3. The composition of claim 2, wherein the nutrient dispersion includes about 10 mM sodium citrate, about 75 mM xylitol, and about 10 mM glutamic acid.

* * * * *